United States Patent [19]

Kawakita et al.

[11] 4,414,216

[45] Nov. 8, 1983

[54] TETRAHYDROFURAN COMPOUNDS AND ANALOGS THEREOF

[75] Inventors: Takeshi Kawakita, Nakatsu; Yasuaki Chihara, Yoshitomi; Takemi Fukuda, Shinyoshitomi; Michihide Setoguchi; Tetsuya Tahara, both of Nakatsu, all of Japan

[73] Assignee: Yoshitomi Phamaceutical Industries, Ltd., Osaka, Japan

[21] Appl. No.: 390,433

[22] Filed: Jun. 21, 1982

[30] Foreign Application Priority Data

Jun. 19, 1981 [JP] Japan 56-95744

[51] Int. Cl.³ .............. A61K 31/505; A61K 31/445; C07D 405/14
[52] U.S. Cl. .................................. 424/251; 424/267; 544/312; 546/20; 546/199; 549/497; 549/504
[58] Field of Search .................. 544/312; 546/20, 199; 424/251, 267

[56] References Cited

U.S. PATENT DOCUMENTS 3,845,060 10/1974 Huebner ............................... 546/20
4,148,796 4/1979 Yamamoto et al. ................ 546/199
4,264,613 4/1981 Regnier et al. ..................... 546/199
4,329,353 5/1982 Stokbroeky et al. ................ 546/20

Primary Examiner—Paul M. Coughlan, Jr.
Attorney, Agent, or Firm—Sughrue, Mion, Zinn, Macpeak and Seas

[57] ABSTRACT

There are disclosed tetrahydrofuran compounds and analogs thereof of the formula:

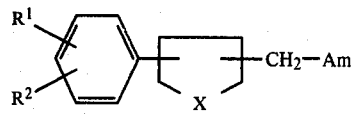

and pharmaceutically acceptable acid addition salts thereof, wherein X is oxygen or sulfur, $R^1$ and $R^2$ are each hydrogen, halogen, lower alkyl or lower alkoxy, and Am is a group of the formula:

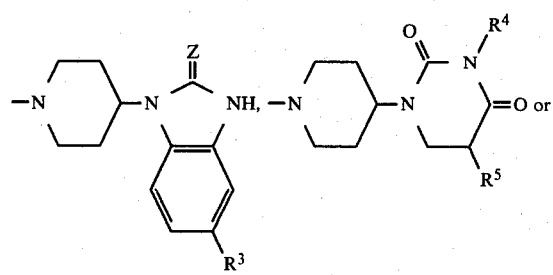

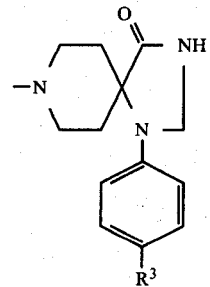

wherein Z is oxygen or sulfur, $R^3$ is hydrogen or halogen, $R^4$ is hydrogen, lower alkyl or phenyl which may be substituted by 1 to 3 substituents at any position(s) on the phenyl nucleus, each substituent being independently selected from halogen, lower alkyl and lower alkoxy, and $R^5$ is hydrogen or lower alkyl. Such compounds are useful as neuroleptics.

10 Claims, No Drawings

TETRAHYDROFURAN COMPOUNDS AND ANALOGS THEREOF

This invention relates to novel and therapeutically valuable tetrahydrofuran compounds and analogs thereof of the formula:

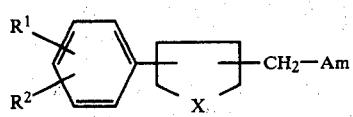
(I)

and pharmaceutically acceptable acid addition salts thereof, wherein X is oxygen atom or sulfur atom, $R^1$ and $R^2$ are each hydrogen atom, halogen atom, lower alkyl group or lower alkoxy group, and Am is an amine residue of the formula:

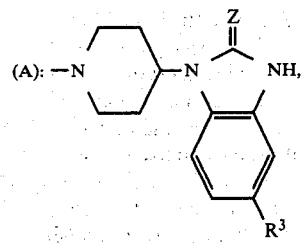

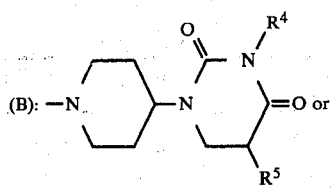

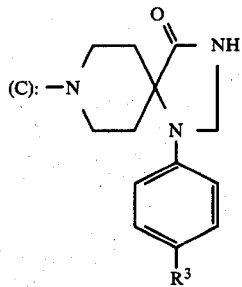

wherein Z is oxygen atom or sulfur atom, $R^3$ is hydrogen atom or halogen atom, $R^4$ is hydrogen atom, lower alkyl group or phenyl group which may be substituted by one to three substituents at any position(s) on the phenyl nucleus, each substituent being independently selected from halogen atom, lower alkyl group and lower alkoxy group, and $R^5$ is hydrogen atom or lower alkyl group.

In the above definitions, the halogen atom includes fluorine, chlorine and bromine, the lower alkyl group includes methyl, ethyl, propyl, isopropyl and butyl, and the lower alkoxy group includes methoxy, ethoxy, propoxy, isopropoxy and butoxy.

The compounds of formula (I) can be produced by reacting a compound of the formula:

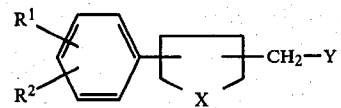
(II)

wherein X, $R^1$ and $R^2$ are as defined above, and Y is halogen atom (e.g. Cl, Br or I) or organic sulfonyloxy group (e.g. tosyloxy or mesyloxy), with an amine compound of the formula: H-Am (III) wherein Am is as defined above.

The reaction is usually carried out in an inert solvent such as methanol, ethanol, isopropanol, benzene, toluene, xylene, dimethylformamide, chloroform, dichloroethane, acetone, methyl ethyl ketone or dimethyl sulfoxide, in the presence of an acid acceptor such as potassium carbonate, sodium carbonate or triethylamine, at a temperature of from room temperature to about 140° C., preferably about 50° to 110° C., for 1 to 48 hours. When Y is other than iodine, the reaction may be accelerated by the use of a catalyst such as potassium iodide or sodium iodide.

The compounds of formula (I) where Am is an amine residue of formula (A) can also be produced by reacting a compound of the formula:

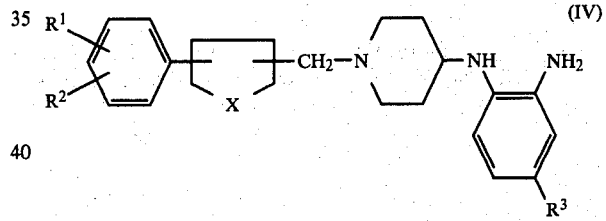
(IV)

wherein X, $R^1$, $R^2$ and $R^3$ are as defined above, with, when Z is oxygen, an alkali metal cyanate (e.g. potassium cyanate or sodium cyanate) in a lower alkanol (e.g. ethanol, isopropanol or butanol) at room temperature to a refluxing temperature, or with, when Z is sulfur, carbon disulfide in the presence of an alkali metal hydroxide (e.g. sodium hydroxide or potassium hydroxide) in a lower alkanol such as mentioned above at room temperature to a refluxing temperature.

The starting materials of formula (IV) can be prepared by the following reaction scheme in accordance with the methods disclosed in Japanese Patent Publication No. 7267/1972.

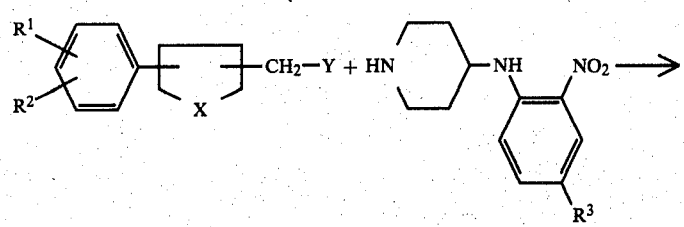

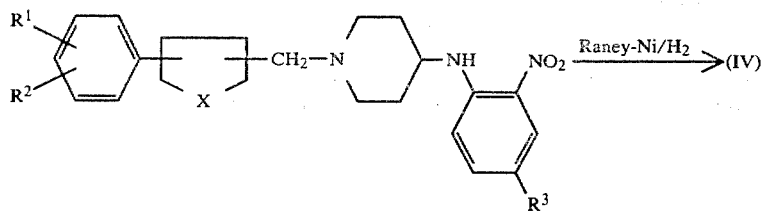

wherein X, $R^1$, $R^2$, Y and $R^3$ are as defined above.

The present invention embraces all kinds of existing stereoisomers as well as tautomers. The stereoisomers may be present as individual optical isomers, cis- and trans-isomers containing one pair of optical isomers and mixtures of four kinds of diastereoisomers. A mixture of stereoisomers, if desired, may be separated into the cis- and trans-diastereoisomers or the individual optical isomers in a conventional manner. The compounds of formula (I) can also be produced stereo-selectively.

The compounds of formula (I) can form pharmaceutically acceptable acid addition salts with various inorganic and organic acids such as hydrochloric, sulfuric, phosphoric, methanesulfonic, maleic, fumaric, oxalic, succinic, acetic, lactic and citric acids.

The compounds of formula (I) and pharmaceutically acceptable acid addition salts thereof show potent neuroleptic effects such as effect on spontaneous locomotor activity, antiapomorphine effect, effect on reserpine potentiation and antinoradrenaline effect, but show weak cataleptogenic activity.

PHARMACOLOGICAL PROPERTIES

1. Test Compounds

A: 1-[1-(2-(4-fluorophenyl)-tetrahydro-4-furylmethyl)-4-piperidyl]benzimidazoline-2-thione hydrochloride B: 1-[1-(2-(4-fluorophenyl)-tetrahydro-4-furylmethyl)-4-piperidyl]benzimidazolin-2-one hydrochloride C: 8-[2-(4-fluorophenyl)-tetrahydro-4-furylmethyl]-1-phenyl-1,3,8-triazaspiro[4.5]decan-4-one maleate D: 1-[1-(2-(4-fluorophenyl)-tetrahydro-4-furylmethyl)-4-piperidyl]hexahydro-2,4-dioxo-3-phenylpyrimidine hydrochloride E: 1-[1-(2-(4-fluorophenyl)-tetrahydro-4-furylmethyl)-4-piperidyl]-5-chloro-benzimidazolin-2-one maleate.

F: 1-[1-(cis-2-(4-fluorophenyl)-tetrahydro-4-furylmethyl)-4-piperidyl]-5-chloro-benzimidazolin-2-one maleate G: 1-[1-(trans-2-(4-fluorophenyl)-tetrahydro-4-furylmethyl)-4-piperidyl]-5-chloro-benzimidazolin-2-one maleate H: 1-[1-(2-(4-fluorophenyl)-tetrahydro-5-furylmethyl)-4-piperidyl]-5-chloro-benzimidazolin-2-one maleate

2. Methods and Results

Antiapomorphine effect was measured by the following methods.

(1) Experiment 1

Motor activity was measured with Automex (Columbus Instruments, U.S.A.) in two groups of 3 male dd mice. Thirty minutes after intraperitoneal administration of each test compound (30 mg/kg), 0.5 mg/kg of apomorphine hydrochloride was injected subcutaneously. Immediately after the apomorphine injection, the animals were placed in the transparent plastic cage (26×42×20 cm) and motor activity during 30 minutes was measured. Student's was calculated to indicate the level of significance of the change from control. The results are shown in Table 1.

(2) Experiment 2

Motor activity was measured with Animex (Columbus Instruments, U.S.A.) in three groups of 5 male dd mice. Sixty minutes after oral administration of each test compound, 0.5 mg/kg of apomorphine hydrochloride was injected subcutaneously. The measurement of motor activity during 20 minutes started just after the apomorphine injection. $ED_{50}$ was determined graphically as the dose which reduced the motor activity by 50% as compared with control. The results are shown in Table 1.

TABLE 1

| Test Compound | Experiment 1 Motor Activity | Experiment 2 $ED_{50}$ |
| --- | --- | --- |
| A | 1 | 3.2 |
| B | 4 | 2.8 |
| C | 0 | 1.4 |
| D | 28 | 25 |
| E | 23 | 0.4 |
| F | 5 | 2.4 |
| G | 8 | 0.9 |
| H | 5 | 12 |
| Control | 566 | — |

In view of various tests including those mentioned above, the compounds of the invention represented by formula (I), in base or salt form, can be safely administered as neuroleptics for the treatment of schizophrenia, in the form of a pharmaceutical preparation with a suitable and conventional pharmaceutically acceptable carrier, without adversely affecting the patients.

The pharmaceutical preparations can take any conventional form such as tablets, capsules, granules, powders or injectable solutions.

The following is an example of formulations when a compound of the invention is administered for pharmaceutical purposes:

Tablets (1 mg) are prepared from the following compositions:

| | |
| --- | --- |
| Compound I or its salt | 1 mg |
| Lactose | 62 mg |
| Microcrystalline cellulose | 15 mg |
| Cornstarch | 20 mg |
| Polyvinyl alcohol | 1.5 mg |
| Magnesium stearate | 0.5 mg |
| | 100 mg |

A compound (I) or its salt, lactose, microcrystalline cellulose and cornstarch are mixed together and then the mixture is kneaded with 5% polyvinyl alcohol. The resulting mixture is granulated and dried, and the dry granules are passed through 24-mesh screen. The fine granules are mixed with magnesium stearate to form granules for the preparation of tablets. The tablets are prepared by compressing the granules on punches (6.5 mm, 7.0 R).

The daily dose of the compound of the invention for human adults usually ranges from about 0.005 mg/kg to about 100 mg/kg, preferably 0.01–50 mg/kg, in single or multiple dose, but it may vary depending upon the age, body weight, and/or severity of the conditions to be treated as well as the response to the medication.

The present invention will be better understood from the following preparative examples (preparation of starting materials of formula (II)) and examples, but they are not to be construed as limiting the present invention.

PREPARATIVE EXAMPLE A 48 g of sodium hydride (60% in mineral oil) is washed three times with hexane, and suspended in 1.5 liters of dry ether. To the stirred suspension are added 180 g of γ-(4-fluorophenyl)-γ-butyrolactone and 81 g of ethyl formate whereupon 5 ml of absolute ethanol is added dropwise. The reaction begins immediately, the boiling ceases in about 10 minutes, and the reaction mixture is allowed to stand. The crystalline precipitate is collected by filtration, washed with dry ether, and dried under reduced pressure to give 230 g of hygroscopic sodium salt of α-formyl-γ-(4-fluorophenyl)-γ-butyrolactone.

To a suspension of 200 g of sodium salt of α-formyl-γ-(4-fluorophenyl)-γ-butyrolactone in 1.5 liters of methanol is added slowly 70 g of sodium borohydride with stirring. The mixture is stirred at room temperature for 18 hours, and the methanol is then distilled off under reduced pressure. The residue is dissolved in 1 liter of water, and the solution is adjusted to pH 1 with concentrated sulfuric acid and heated under reflux for 1 hour. After cooling, the solution is adjusted to pH 11–12 with 40% aqueous sodium hydroxide solution, and stirred at 50° C. for 2 hours and then cooled. The reaction mixture is extracted twice with ethyl acetate. The combined extracts are washed with water and dried over magnesium sulfate, and the solvent is distilled off under reduced pressure. The residue is distilled to give 71 g of 2-(4-fluorophenyl)-4-(hydroxymethyl)tetrahydrofuran as colorless oil, boiling at 120°–126° C. (0.06 mmHg).

PREPARATIVE EXAMPLE B 2-(4-Fluorophenyl)-4-(hydroxymethyl)tetrahydrofuran (21 g) is dissolved in 170 ml of pyridine whereupon 24.4 g of tosyl chloride is added below 4° C., and the resulting mixture is stirred at 4° C. for 1 hour and then at room temperature for 4 hours. The pyridine is then distilled off at room temperature under reduced pressure. Water is added to the residue and extracted with ethyl acetate. The extract is washed twice with dilute hydrochloric acid and once with water and dried over magnesium sulfate, and the solvent is distilled off under reduced pressure. To the residue are added n-hexane and isopropyl ether to give 32.7 g of 2-(4-fluorophenyl)-4-(tosyloxymethyl)tetrahydrofuran. This tosyl compound is recrystallized repeatedly from isopropanol to give cis-2-(4-fluorophenyl)-4-tosyloxymethyl)tetrahydrofuran as colorless needles, melting at 75°–76.5° C., and recrystallized from ethanol to give the trans-isomer as colorless needles, melting at 55°–57° C.

PREPARATIVE EXAMPLE C

A mixture of 9.2 g of trans-2-(4-fluorophenyl)-4-(tosyloxymethyl)tetrahydrofuran and 12.6 g of sodium iodide in 130 ml of acetone is heated under reflux for 6 hours. The solvent is then distilled off under reduced pressure, and the residue is extracted with ether. The extract is washed with water and dried over magnesium sulfate, and the solvent is distilled off to give a quantitative yield of trans-2-(4-fluorophenyl)-4-(iodomethyl)tetrahydrofuran as colorless oil, $n_D^{27}$ 1.5675.

PREPARATIVE EXAMPLE D

4-Cyano-4-phenyl-1-butene (15 g) is dissolved in 50 ml of ethanol and 3 drops of water whereupon 20 ml of sulfuric acid is added dropwise. The resulting mixture is warmed slowly and then heated under reflux for 6 hours. The reaction mixture is then poured into 100 ml of ice-cold water and extracted with 100 ml of benzene. The extract is dried over magnesium sulfate, and the solvent is distilled off under reduced pressure. The residue is distilled to give 7.0 g of ethyl 2-phenyl-4-pentenoate, boiling at 133°–137° C. (20 mmHg).

A solution of 6.0 g of ethyl 2-phenyl-4-pentenoate in 10 ml of tetrahydrofuran is added dropwise to a stirred suspension of 2.0 g of lithium aluminum hydride in 40 ml of tetrahydrofuran at room temperature. The resulting mixture is stirred at 40°–45° C. for 2 hours. Under ice-cooling, water (10 ml) is added dropwise to the reaction mixture in order to decompose the unreacted lithium aluminum hydride. The mixture is poured into 200 ml of ice-cold water and extracted with 200 ml of benzene. The extract is washed with water and dried over magnesium sulfate, and the solvent is distilled off under reduced pressure. The residue is purified by column chromatography on silica gel with chloroform eluate to give 2.4 g of 2-phenyl-4-penten-1-ol as colorless oil.

N-Bromosuccinimide (1.78 g) is added to a stirred solution of 1.6 g of 2-phenyl-4-penten-1-ol in 15 ml of chloroform at room temperature. The resulting mixture is stirred at room temperature for 3 hours. The reaction mixture is then poured into 10 ml of water. The chloroform layer is separated and dried over magnesium sulfate, and the solvent is distilled off under reduced pressure. The residue is purified by column chromatography on silica gel with chloroform eluant to give 1.67 g of 2-(bromomethyl)-4-phenyltetrahydrofuran as colorless oil.

PREPARATIVE EXAMPLE E

A mixture of 7.4 g of 1-(4-fluorophenyl)-4-penten-1-ol and 8.0 g of N-bromosuccinimide in 100 ml of chloroform is stirred at room temperature for 3 hours. The reaction mixture is then washed with water and dried over magnesium sulfate, and the solvent is distilled off under reduced pressure. The residue is purified by column chromatography on silica gel with chloroform eluant to give 9.8 g of 2-(4-fluorophenyl)-5-(bromomethyl)tetrahydrofuran as colorless oil, $n_D^{27}$ 1.5218.

EXAMPLE 1

A mixture of 5.0 g of trans-2-(4-fluorophenyl)-4-(iodomethyl)tetrahydrofuran, 4.2 g of 1-(4-piperidyl)-benzimidazolin-2-one and 2.5 g of potassium carbonate in 80 ml of dimethylformamide is heated with stirring at 60°–70° C. for 42 hours. The reaction mixture is then poured into water and extracted with ethyl acetate. The extract is washed three times with water and dried over magnesium sulfate, and the solvent is distilled off under reduced pressure. Isopropyl ether is added to the residue, and the crystals precipitated are collected by filtration and recrystallized from ethanol to give 5.1 g of 1-[1-(trans-2-(4-fluorophenyl)-tetrahydro-4-furylmethyl)-4-piperidyl]benzimidazolin-2-one as colorless needles, melting at 154°–155° C. The corresponding hydrochloride melts at 239° C. with decomposition.

EXAMPLE 2

A mixture of 2.59 g of 2-(4-fluorophenyl)-5-(bromomethyl)tetrahydrofuran, 2.17 g of 1-(4-piperidyl)benzimidazolin-2-one, 1.5 g of sodium iodide and 1.38 g of potassium carbonate in 30 ml of dimethylformamide is heated with stirring at 50°–60° C. for 3 hours. The reaction mixture is then poured into water and extracted with chloroform. The extract is washed twice with water and dried over magnesium sulfate, and the solvent is distilled off under reduced pressure. The residue is purified by column chromatography on silica gel with chloroform eluant. The thus obtained colorless oil is dissolved in ethanol, and fumaric acid is added thereto. The crystals precipitated are collected by filtration and recrystallized from ethanol to give 1-[1-(2-(4-fluorophenyl)-tetrahydro-5-furylmethyl)-4-piperidyl]-benzimidazolin-2-one fumarate as colorless needles, melting at 200°–201° C.

EXAMPLE 3

A mixture of 5.2 g of trans-2-(4-fluorophenyl)-4-(iodomethyl)tetrahydrofuran, 4.3 g of 1-(4-piperidyl)-5-chloro-benzimidazolin-2-one and 2.3 g of potassium carbonate in 50 ml of dimethylformamide is heated with stirring at 70° C. for 24 hours. The reaction mixture is then poured into water and extracted with ethyl acetate. The extract is washed with water and dried over magnesium sulfate, and the solvent is distilled off under reduced pressure. The residue is dissolved in a small amount of chloroform, and a solution of 0.8 g of maleic acid in ethanol is added thereto. The crystals precipitated are collected by filtration and recrystallized from methanol to give 1-[1-(trans-2-(4-fluorophenyl)-tetrahydro-4-furylmethyl)-4-piperidyl]-5-chloro-benzimidazolin-2-one maleate, melting at 208.5°–209° C.

EXAMPLE 4

A mixture of 1.74 g of cis-2-(4-fluorophenyl)-4-(iodomethyl)tetrahydrofuran, 1.5 g of 1-(4-piperidyl)-5-chloro-benzimidazolin-2-one and 0.8 g of potassium carbonate in 20 ml of dimethylformamide is heated with stirring at 70° C. for 16 hours. The reaction mixture is then poured into water and extracted with ethyl acetate. The extract is washed with water and dried over magnesium sulfate, and the solvent is distilled off under reduced pressure. The crystalline residue is recrystallized from ethanol to give 1-[1-(cis-2-(4-fluorophenyl)-tetrahydro-4-furylmethyl)-4-piperidyl]-5-chloro-benzimidazolin-2-one as colorless prisms, melting at 207.5°–208.5° C. The corresponding maleate melts at 207° C. with decomposition.

EXAMPLE 5

A mixture of 3.1 g of 4-(4-fluorophenyl)-2-(bromomethyl)tetrahydrofuran, 3.5 g of 1-(4-piperidyl)-5-chloro-benzimidazolin-2-one, 2.5 g of sodium iodide and 2.0 g of potassium carbonate in 50 ml of dimethylformamide is heated with stirring at 60° C. for 24 hours. The reaction mixture is then poured into water and extracted with ethyl acetate. The extract is washed with water and dried over magnesium sulfate, and the solvent is distilled off under reduced pressure. The residue is purified by column chromatography on silica gel with chloroform eluant. The thus obtained oil is treated with maleic acid. The crystalline precipitate is collected by filtration and recrystallized from ethanol to give 1-[1-(4-(4-fluorophenyl)-tetrahydro-2-furylmethyl)-4-piperidyl]-5-chloro-benzimidazolin-2-one maleate, melting at 200°–201° C. with decomposition.

EXAMPLE 6

A mixture of 9.56 g of 1-[cis-2-(4-fluorophenyl)-tetrahydro-4-furylmethyl]-4-(2-aminoanilino)piperidine trihydrochloride and 2.0 g of potassium cyanate in 100 ml of ethanol is heated under reflux with stirring for 8 hours. The ethanol is then distilled off under reduced pressure, and 10 ml of 10% aqueous sodium hydroxide solution and 50 ml of water are added to the residue and extracted with ethyl acetate. The extract is washed with water and dried over magnesium sulfate, and the solvent is distilled off under reduced pressure. The residue is dissolved in a small amount of ethanol, and ethanolic hydrochloric acid is added thereto. The crystals precipitated are collected by filtration and recrystallized from ethanol-water to give 1-[1-(cis-2-(4-fluorophenyl)-tetrahydro-4-furylmethyl)-4-piperidyl]benzimidazolin-2-one hydrochloride, melting at 276° C. with decomposition.

EXAMPLE 7

A mixture of 13.7 g of 1-[2-(4-fluorophenyl)-tetrahydro-4-furylmethyl]-4-(2-aminoanilino)piperidine, 18 g of carbon disulfide and 4.2 g of potassium hydroxide is heated under reflux with stirring for 3.5 hours and then cooled. To the mixture are added 200 ml of ethanol, 126 ml of water and 32 ml of concentrated hydrochloric acid, and the whole is heated under reflux for 20 minutes. The solvent is then distilled off under reduced pressure. The residue is made alkaline with aqueous ammonia and extracted with ethyl acetate. The extract is washed with water and dried over magnesium sulfate, and the solvent is distilled off under reduced pressure. The residue is purified by column chromatography on silica gel with chloroform eluant. To the thus obtained oil is added ethanolic hydrochloric acid. The crystals precipitated are collected by filtration and recrystallized from methanol-isopropyl ether to give 1-[1-(2-(4-fluorophenyl)-tetrahydro-4-furylmethyl)-4-piperidyl]-benzimidazoline-2-thione hydrochloride as colorless needles, melting at 269°–270° C. with decomposition.

EXAMPLE 8

A mixture of 6.0 g of 2-(4-fluorophenyl)-4-(iodomethyl)tetrahydrofuran, 5.5 g of 1-(4-piperidyl)-hexahydro-2,4-dioxo-3-phenylpyrimidine and 2.8 g of potassium carbonate in 100 ml of dimethylformamide is heated with stirring at 60° C. for 22 hours. The reaction mixture is then poured into water and extracted with ethyl acetate. The extract is washed with water and dried over magnesium sulfate, and the solvent is distilled off under reduced pressure. The crystalline residue is treated with ethanolic hydrochloric acid and recrystallized from ethanol-water to give 1-[1-(2-(4-fluorophenyl)-tetrahydro-4-furylmethyl)-4-piperidyl]-hexahydro-2,4-dioxo-3-phenylpyrimidine hydrochloride, melting at 274° C. with decomposition.

EXAMPLE 9

A mixture of 4.0 g of 2-bromomethyl-4-phenyltetrahydrofuran, 3.83 g of 1-phenyl-1,3,8-triazaspiro[4.5]decan-4-one, 2.48 g of sodium iodide and 2.3 g of potassium carbonate in 50 ml of dimethylformamide is heated with stirring at 60° C. for 24 hours. The reaction mixture is then poured into 200 ml of water, and 50 ml of ethyl acetate is added thereto. The mixture is stirred under ice-cooling. The crystals precipitated are collected by filtration, treated with maleic acid and recrystallized from ethanol to give 8-(4-phenyl-tetrahydro-2-furylmethyl)-1-phenyl-1,3,8-triazaspiro[4.5]decan-4-one maleate, melting at 202°–204° C. with decomposition.

EXAMPLE 10

A mixture of 3.2 g of 2-(4-fluorophenyl)-4-(iodomethyl)tetrahydrofuran, 2.4 g of 1-phenyl-1,3,8-triazaspiro[4.5]decan-4-one and 1.4 g of potassium carbonate in 60 ml of dimethylformamide is heated with stirring at 70° C. for 21 hours. The reaction mixture is then poured into water and extracted with ethyl acetate. The extract is washed with water and dried over magnesium sulfate, and the solvent is distilled off under reduced pressure. The residue is purified by column chromatography on silica gel with chloroform eluant. The thus obtained purified crystals are treated with maleic acid and recrystallized from ethanol-water to give 8-[2-(4-fluorophenyl)-tetrahydro-4-furylmethyl]-1-phenyl-1,3,8-triazaspiro[4.5]-decan-4-one maleate, melting at 175° C. with decomposition.

Using the procedures set forth in the above examples, the following compounds are also produced:

(1) 1-[1-(2-(4-fluorophenyl)-tetrahydro-4-furylmethyl)-4-piperidyl]-benzimidazolin-2-one hydrochloride, m.p. 260° C. (decomposition)
(2) 1-[1-(2-(4-fluorophenyl)-tetrahydro-4-furylmethyl)-4-piperidyl]-5-chloro-benzimidazolin-2-one maleate, m.p. 217° C. (decomposition)
(3) 1-[1-(2-(4-fluorophenyl)-tetrahydro-4-furylmethyl)-4-piperidyl]-5-chloro-benzimidazoline-2-thione 1/2-maleate, m.p. 211° C. (decomposition)
(4) 1-[1-(2-(4-fluorophenyl)-tetrahydro-5-furylmethyl)-4-piperidyl]-5-chloro-benzimidazolin-2-one maleate, m.p. 188°–190° C. (decomposition)
(5) 1-[1-(4-phenyl-tetrahydro-2-furylmethyl)-4-piperidyl]-5-chlorobenzimidazolin-2-one maleate, m.p. 217°–218° C. (decomposition)
(6) 1-[1-(2-phenyl-tetrahydro-4-furylmethyl)-4-piperidyl]benzimidazolin-2-one
(7) 1-[1-(2-(4-chlorophenyl)-tetrahydro-4-furylmethyl)-4-piperidyl]-benzimidazolin-2-one
(8) 1-[1-(2-(4-methoxyphenyl)-tetrahydro-4-furylmethyl)-4-piperidyl]-benzimidazolin-2-one
(9) 1-[1-(2-(2-chlorophenyl)-tetrahydro-4-furylmethyl)-4-piperidyl]-benzimidazolin-2-one
(10) 1-[1-(4-(4-fluorophenyl)-tetrahydro-2-furylmethyl)-4-piperidyl]-benzimidazolin-2-one
(11) 1-[1-(3-(4-fluorophenyl)-tetrahydro-4-furylmethyl)-4-piperidyl]-benzimidazolin-2-one
(12) 1-[1-(2-(4-fluorophenyl)-tetrahydro-4-thienylmethyl)-4-piperidyl]-benzimidazolin-2-one
(13) 1-[1-(2-(4-fluorophenyl)-tetrahydro-4-thienylmethyl)-4-piperidyl]-5-chloro-benzimidazolin-2-one
(14) 1-[1-(2-phenyl-tetrahydro-5-thienylmethyl)-4-piperidyl]benzimidazolin-2-one
(15) 1-[1-(2-(4-fluorophenyl)-tetrahydro-5-thienylmethyl)-4-piperidyl]-benzimidazolin-2-one
(16) 1-[1-(2-(4-fluorophenyl)-tetrahydro-5-thienylmethyl)-4-piperidyl]-benzimidazoline-2-thione
(17) 1-[1-(2-(4-fluorophenyl)-tetrahydro-5-thienylmethyl)-4-piperidyl]-5-chloro-benzimidazolin-2-one
(18) 1-[1-(4-(4-fluorophenyl)-tetrahydro-2-thienylmethyl)-4-piperidyl]-benzimidazolin-2-one
(19) 1-[1-(2-(p-tolyl)-tetrahydro-4-furylmethyl)-4-piperidyl]benzimidazolin-2-one
(20) 1-[1-(2-(3,4-dimethoxyphenyl)-tetrahydro-4-furylmethyl)-4-piperidyl]-benzimidazolin-2-one
(21) 1-[1-(2-(4-fluorophenyl)-tetrahydro-4-furylmethyl)-4-piperidyl]-hexahydro-2,4-dioxopyrimidine fumarate, m.p. 127° C.
(22) 1-[1-(2-(4-fluorophenyl)-tetrahydro-4-furylmethyl)-4-piperidyl]-hexahydro-3-methyl-2,4-dioxopyrimidine hydrochloride, m.p. 217° C. (decomposition)
(23) 1-[1-(2-(4-fluorophenyl)-tetrahydro-5-furylmethyl)-4-piperidyl]-hexahydro-2,4-dioxo-3-phenylpyrimidine fumarate hemihydrate, m.p. 193°–196° C.
(24) 1-[1-(2-(4-fluorophenyl)-tetrahydro-4-furylmethyl)-4-piperidyl]-hexahydro-5-methyl-2,4-dioxo-3-phenylpyrimidine, m.p. 164° C.
(25) 1-[1-(2-phenyl-tetrahydro-4-furylmethyl)-4-piperidyl]-hexahydro-2,4-dioxo-3-phenylpyrimidine
(26) 1-[1-(2-(4-chlorophenyl)-tetrahydro-4-furylmethyl)-4-piperidyl]-hexahydro-2,4-dioxo-3-phenylpyrimidine
(27) 1-[1-(2-(4-methoxyphenyl)-tetrahydro-4-furylmethyl)-4-piperidyl]-hexahydro-2,4-dioxo-3-phenylpyrimidine hydrochloride hemihydrate, m.p. 219° C. (decomposition)
(28) 1-[1-(2-(2-chlorophenyl)-tetrahydro-4-furylmethyl)-4-piperidyl]-hexahydro-2,4-dioxo-3-phenylpyrimidine
(29) 1-[1-(4-(4-fluorophenyl)-tetrahydro-2-furylmethyl)-4-piperidyl]-hexahydro-2,4-dioxo-3-phenylpyrimidine
(30) 1-[1-(2-(4-fluorophenyl)-tetrahydro-4-furylmethyl)-4-piperidyl]-hexahydro-3-(4-chlorophenyl)-2,4-dioxopyrimidine, m.p. 172°–175° C.
(31) 1-[1-(2-(4-fluorophenyl)-tetrahydro-4-furylmethyl)-4-piperidyl]-hexahydro-3-(4-methoxyphenyl)-2,4-dioxopyrimidine
(32) 1-[1-(2-(4-fluorophenyl)-tetrahydro-4-furylmethyl)-4-piperidyl]-hexahydro-3-(2-chlorophenyl)-2,4-dioxopyrimidine oxalate, m.p. 93° C. (decomposition)
(33) 1-[1-(2-(4-fluorophenyl)-tetrahydro-4-furylmethyl)-4-piperidyl]-hexahydro-3-(3,4-dimethoxyphenyl)-2,4-dioxopyrimidine
(34) 1-[1-(2-(4-fluorophenyl)-tetrahydro-4-furylmethyl)-4-piperidyl]-hexahydro-3-(p-tolyl)-2,4-dioxopyrimidine, m.p. 178°–181° C.
(35) 1-[1-(2-(4-fluorophenyl)-tetrahydro-4-furylmethyl)-4-piperidyl]-hexahydro-3-(4-fluorophenyl)-2,4-dioxopyrimidine
(36) 1-[1-(2-(4-fluorophenyl)-tetrahydro-4-furylmethyl)-4-piperidyl]-hexahydro-3-(3,4-dichlorophenyl)-2,4-dioxopyrimidine hydrochloride, m.p. 304° C. (decomposition)
(37) 1-[1-(2-(4-fluorophenyl)-tetrahydro-5-furylmethyl)-4-piperidyl]-hexahydro-3-(4-methoxyphenyl)-2,4-dioxopyrimidine

(38) 1-[1-(2-(4-fluorophenyl)-tetrahydro-5-furylmethyl)-4-piperidyl]-hexahydro-3-(4-chlorophenyl)-2,4-dioxopyrimidine

(39) 1-[1-(2-(4-fluorophenyl)-tetrahydro-4-thienylmethyl)-4-piperidyl]-hexahydro-2,4-dioxo-3-phenylpyrimidine

(40) 1-[1-(2-(4-fluorophenyl)-tetrahydro-4-thienylmethyl)-4-piperidyl]-hexahydro-3-(4-chlorophenyl)-2,4-dioxopyrimidine

(41) 1-[1-(2-(4-fluorophenyl)-tetrahydro-5-thienylmethyl)-4-piperidyl]-hexahydro-2,4-dioxo-3-phenylpyrimidine

(42) 1-[1-(2-(4-fluorophenyl)-tetrahydro-5-thienylmethyl)-4-piperidyl]-hexahydro-3-(4-methoxyphenyl)-2,4-dioxopyrimidine

(43) 8-[2-(4-fluorophenyl)-tetrahydro-5-furylmethyl]-1-phenyl-1,3,8-triazaspiro[4.5]decan-4-one maleate, m.p. 220° C. (decomposition)

(44) 8-[4-(4-fluorophenyl)-tetrahydro-2-furylmethyl]-1-phenyl-1,3,8-triazaspiro[4.5]decan-4-one

(45) 8-[2-(4-fluorophenyl)-tetrahydro-4-furylmethyl]-1-(4-bromophenyl)-1,3,8-triazaspiro[4.5]decan-4-one

(46) 8-[2-(4-fluorophenyl)-tetrahydro-5-furylmethyl]-1-(4-bromophenyl)-1,3,8-triazaspiro[4.5]decan-4-one

(47) 8-[2-(4-fluorophenyl)-tetrahydro-4-thienylmethyl]-1-phenyl-1,3,8-triazaspiro[4.5]decan-4-one

(48) 8-[2-(4-fluorophenyl)-tetrahydro-5-thienylmethyl]-1-phenyl-1,3,8-triazaspiro[4.5]decan-4-one

(49) 1-[1-(2-(4-chlorophenyl)-tetrahydro-4-furylmethyl)-4-piperidyl]-5-chloro-benzimidazolin-2-one, m.p. 172°–173° C.

(50) 1-[1-(2-(4-methoxyphenyl)-tetrahydro-4-furylmethyl)-4-piperidyl]-5-chloro-benzimidazolin-2-one maleate, m.p. 233°–235° C. (decomposition)

While the invention has been described in detail and with reference to specific embodiments thereof, it will be apparent to one skilled in the art that various changes and modifications can be made therein without departing from the spirit and scope thereof.

What is claimed is:

1. A compound of the formula:

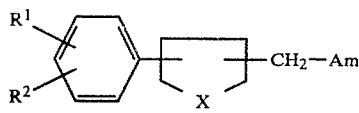

or a pharmaceutically acceptable acid addition salt thereof, wherein X is oxygen atom or sulfur atom, $R^1$ and $R^2$ are each hydrogen atom, halogen atom, lower alkyl group or lower alkoxy group, and Am is a group of the formula:

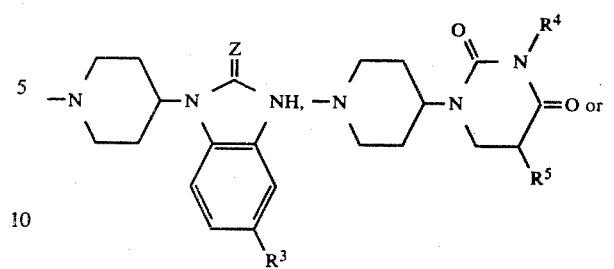

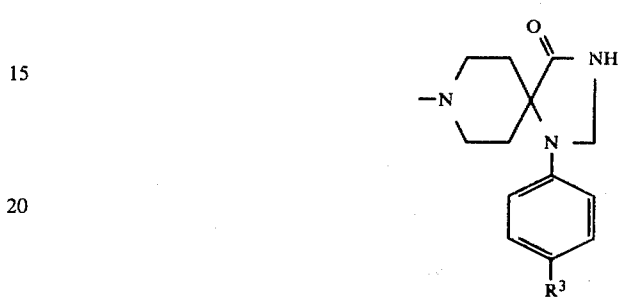

wherein Z is oxygen atom or sulfur atom, $R^3$ is hydrogen atom or halogen atom, $R^4$ is hydrogen atom, lower alkyl group or phenyl group which may be substituted by one to three substituents at any position(s) on the phenyl nucleus, each substituent being independently selected from halogen atom, lower alkyl group and lower alkoxy group, and $R^5$ is hydrogen atom or lower alkyl group.

2. The compound of claim 1: 1-[1-(trans-2-(4-fluorophenyl)-tetrahydro-4-furylmethyl)-4-piperidyl]benzimidazolin-2-one.

3. The compound of claim 1: 1-[1-(trans-2-(4-fluorophenyl)-tetrahydro-4-furylmethyl)-4-piperidyl]-5-chloro-benzimidazolin-2-one.

4. The compound of claim 1: 1-[1-(cis-2-(4-fluorophenyl)-tetrahydro-4-furylmethyl)-4-piperidyl]-5-chloro-benzimidazolin-2-one.

5. The compound of claim 1: 1-[1-(2-(4-fluorophenyl)-tetrahydro-4-furylmethyl)-4-piperidyl]benzimidazoline-2-thione.

6. The compound of claim 1: 1-[1-(2-(4-fluorophenyl)-tetrahydro-5-furylmethyl)-4-piperidyl]-5-chloro-benzimidazolin-2-one.

7. The compound of claim 1: 1-[1-(4-(4-fluorophenyl)-tetrahydro-2-furylmethyl)-4-piperidyl]-5-chloro-benzimidazolin-2-one.

8. The compound of claim 1: 1-[1-(2-(4-fluorophenyl)-tetrahydro-4-furylmethyl)-4-piperidyl]-hexahydro-2,4-dioxo-3-phenylpyrimidine.

9. The compound of claim 1: 8-[2-(4-fluorophenyl)-tetrahydro-4-furylmethyl]-1-phenyl-1,3,8-triazaspiro[4.5]decan-4-one.

10. A pharmaceutical composition comprising the compound of claim 1 in combination with a pharmaceutically acceptable inert carrier, said compound being present in a therapeutically effective amount.

* * * * *